United States Patent [19]

Kirsch et al.

[11] Patent Number: 5,730,743
[45] Date of Patent: Mar. 24, 1998

[54] SUPPORTING GRID

[76] Inventors: Axel Kirsch, Talstrasse 23, D-70772 Filderstadt; Walter Dürr, Panoramastr. 5, D-79196 Remchingen, both of Germany

[21] Appl. No.: 750,032
[22] PCT Filed: May 3, 1995
[86] PCT No.: PCT/DE95/00594
  § 371 Date: Feb. 11, 1997
  § 102(e) Date: Feb. 11, 1997
[87] PCT Pub. No.: WO95/31940
  PCT Pub. Date: Nov. 30, 1995

[30] Foreign Application Priority Data

May 25, 1994 [DE] Germany ............ 44 18 159.0

[51] Int. Cl.⁶ .................................. A61B 17/56
[52] U.S. Cl. ................ 606/69; 606/76; 606/86; 606/215
[58] Field of Search ............... 606/69, 70, 71, 606/60, 72, 76, 77, 86, 213, 215; 433/173, 174

[56] References Cited

U.S. PATENT DOCUMENTS

| 2,580,821 | 1/1952 | Nicola | 606/69 |
| 3,593,709 | 7/1971 | Halloran | 606/69 |
| 3,695,259 | 10/1972 | Yost | 606/69 |
| 3,955,567 | 5/1976 | Richmond et al. | |
| 4,636,215 | 1/1987 | Schwartz | 623/16 |
| 5,139,497 | 8/1992 | Tilghman et al. | |
| 5,380,328 | 1/1995 | Morgan | 606/70 |
| 5,413,577 | 5/1995 | Pollock | 606/69 |
| 5,443,483 | 8/1995 | Kirsch | 606/74 |
| 5,527,311 | 6/1996 | Proctor et al. | 606/61 |
| 5,591,234 | 1/1997 | Kirsch | 623/16 |

FOREIGN PATENT DOCUMENTS

| 2 631 539 | 11/1989 | France . |
| 39 42 675 | 5/1991 | Germany . |
| 91 15 341 U | 4/1992 | Germany . |

*Primary Examiner*—Guy V. Tucker
*Attorney, Agent, or Firm*—Hill, Steadman & Simpson

[57] ABSTRACT

Supporting grid for the mechanical support of a cover membrane, which membrane covers a bone void filled with a bone replacement material such as hydroxyl apatite granules, particularly a recess in the proper bone tissue of the body, characterized in that the supporting grid is bendable around at least one axis predetermined by the fashioning of the supporting grid.

18 Claims, 1 Drawing Sheet

(II-II)

SUPPORTING GRID

This application is filed under 35 USC 371 based on PCT/DE95/00594 which was filed May 3, 1995, published as WO95/31940, Nov. 30, 1995.

BACKGROUND OF THE INVENTION

The invention is directed to a supporting grid for the mechanical support of a cover membrane covering a bone void filled with a bone replacement material such as hydroxyl apatite granules, particularly a recess in the proper bone tissue of the body.

It is standard in osteosurgery, for example in the reconstruction of bones in plastic surgery or in surgical operations of the jaw, to fill bone voids in the form of recesses or cavities in the proper bone tissue of the body with ossiferous material that is usually composed of a mixture of bone replacement material such as hydroxyl apatite granules and proper bone particles of the body. Until a replacement bone has formed from the particulate bone replacement material, such bone voids must be covered with a cover membrane mechanically stabilized by a supporting grid.

DE 91 15 341 U1 discloses a supporting grid for covering particulate bone replacement agents that is composed of a biodegradable and thermoplastically shapable polymer. The supporting grid serves the purpose of enabling a mechanical support of bone replacement material and, for example given complete partition of the lower jaw, fixing the two resection stumps to one another. However, it has only limited flexibility and therefore requires comparatively great outlay in order to be adapted to the contours of the bone to be treated.

SUMMARY OF THE INVENTION

The invention is based on the object of creating a novel supporting grid that overcomes the above-described disadvantages and that can be more precisely adapted to the bone under treatment, particularly the jaw bone, with less outlay.

The invention is therefore based on the object of improving the supporting grid to such effect that a faultless adaptation of the supporting grid to the shape of the bone void and the proper bone of the body surrounding it is assured.

In a development of the supporting grid of the species, this object is achieved in that the supporting grid is bendable around at least one axis predetermined by the fashioning of the supporting grid.

It is thereby inventively provided that the outside contour of the unbent supporting grid essentially corresponds to that of an annulus sector.

The invention further provides that the supporting grid is bendable around at least one axis that is concentric with the outside arc of the annulus sector and located in the plane of the bent-over supporting grid.

Over and above this, it is proposed that the supporting grid is bendable around an axis perpendicular to and outside the plane of the bent-over supporting grid.

It is provided in a further development of the invention that the supporting grid comprises recesses or slots along the inside arc and along the outside arc of the annulus sector.

The recesses or slots along the inside arc are preferably arranged offset relative to the recesses or slots along the outside arc.

The invention also proposes that the recesses or slots along the inside arc and the recesses or slots along the outside arc respectively comprise a uniform shape.

The invention also provides that the shape of the recesses or slots along the inside arc differs from the shape of the recesses or slots along the outside arc.

The recesses or slots at the inside arc and at the outside arc each preferably comprise a radial symmetry axis.

It is provided in an advantageous development of the novel supporting grid that the recesses or slots at the inside arc are broader transversely to the radial symmetry axis in the immediate proximity of said inside arc than the recesses or slots at the outside arc in the immediate proximity thereof.

It is also proposed that the recesses or slots at the outside arc are fashioned radially inwardly concave from the outside contour and then conically tapering.

The invention further provides that the recesses or slots at the inside arc are fashioned initially essentially hose-like radially outward from the inside contour, then expanding comparatively slightly in circular fashion and then in turn tapering down to a minimum width, hose-like again over a comparatively small region and then, finally, expanding greatly and subsequently tapering conically.

The bases of the conical sections of the recesses or slots at the inside arc are preferably located on nearly the same radius as the tips of the conical sections of the recesses or slots at the outside arc.

The invention further provides that the supporting grid comprises sub-recesses or secondary slots along the inside and outside arc that are open toward the outside contour.

The invention is based on the surprising perception that one succeeds in eliminating the difficulties that still exist in the application of the supporting grid of the species in certain application in that the supporting grid comprises a grid structure that allows the production of the spherical structures needed for the adaptation to bone contours.

The novel supporting grid improves and facilitates the adaptation to the contours of the bone under treatment and even allows the preparation of a preliminary model to foregone in certain instances.

It is thereby especially beneficial, for example in view of the support of bone voids in the jaw bone, when the supporting grid, as provided in an embodiment of the invention, is bendable around an axis perpendicular to and outside the plane of the unbent supporting grid.

Further features and advantages of the invention derive from the claims and from the following description, in which an exemplary embodiment is described in detail with reference to the schematic drawings.

DESCRIPTION OF THE PREFERRED EMBODIMENTS

Figure 1:
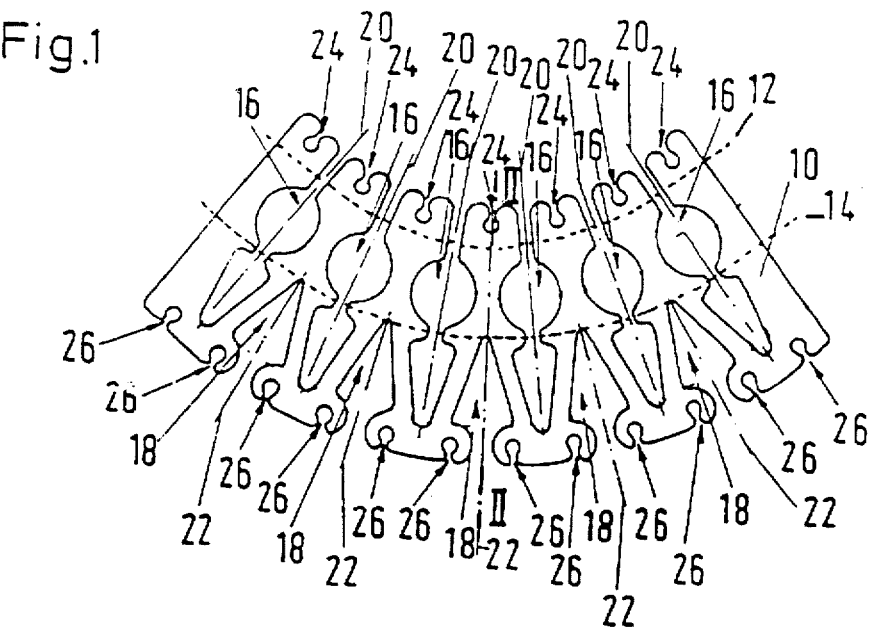
FIG. 1 is a plan view of an unbent supporting grid.

FIG. 1 shows a supporting grid 10 whose outside contour describes an annulus sector. Recesses or slots 16 and 18 are located both at the inside arc as well as at the outside arc of the annulus sector. The recesses 16 along the inside arc are arranged offset relative to the recesses 18 along the outside arc and each respectively comprise a uniform shape. The shape of the recesses 16 along the inside arc differs from the shape of the recesses 18 along the outside arc. The recesses 16 and 18 each comprise a radial symmetry axis 20 or, respectively, 22. The recesses at the inside arc in the immediate proximity thereof transverse to the radial symmetry axis 20 are broader than the recesses 18 at the outside arc in the immediate proximity thereof. Whereas the recesses 18 at the outside arc are fashioned radially inwardly concave proceeding from the outside contour and then conically tapering, the recesses 16 at the inside arc are fashioned initially essentially hose-like or as a narrow slot or channel with parallel edges radially outward from the inside contour, then expanding comparatively slightly in circular fashion and then in turn tapering down to a minimum width channel or slot again over a small region and then, finally, expanding greatly and subsequently tapering conically. The bases of the conical sections of the recesses or slots 16 at the inside arc are located on nearly the same radius as the tips of the conical sections of the recesses or slots 18 at the outside arc. Over and above this, the supporting grid 10 comprises sub-recesses or supplementary slots 24 and 26 along the inside arc and along the outside arc that are open toward the outside contour. Due to the shaping and the arrangement of the recesses 16 and 18, the supporting grid is bendable around two axes 12 and 14 that are situated concentric with the outside arc and in the plane of the supporting grid 10.

Figure 2:
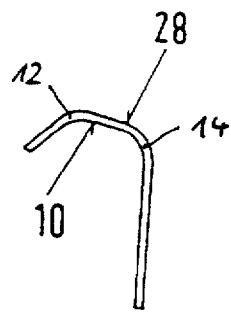
FIG. 2 is a cross sectional view taken along the line II—II of the supporting grid of FIG. 1 in the bent condition.

FIG. 2 shows the bent structure 10 in section along the line II—II. For the sake of completeness, FIG. 2 also shows a cover membrane 28 carried by the supporting grid, this cover membrane having been omitted from FIGS. 1 and 3 for the sake of clarity. Due to the fashioning and arrangement of the slots, notches or recesses, the bending axes are predetermined in the plane of the supporting grid and yield the bend pattern shown in FIG. 2. The structure of the supporting grid 10 also makes it possible to additionally bend the supporting grid 10 around an axis perpendicular to and outside the plane of the supporting grid 10. This exemplary embodiment is thus particularly suited for the support of bone voids in jaw bones.

Figure 3:
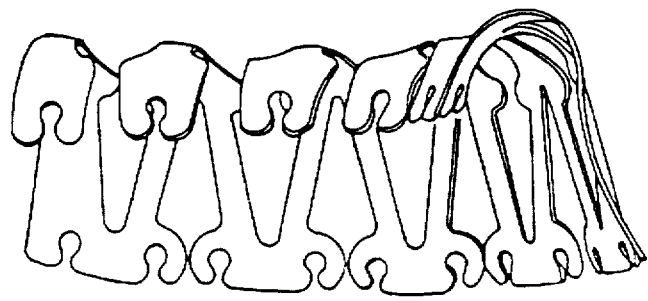
FIG. 3 is a perspective view of the bent supporting grid of FIG. 1.

The perspective view in FIG. 3 illustrates the good adaptability of this exemplary embodiment to a jaw bone.

Both individually as well as in arbitrary combinations, the features of the invention disclosed in the above description, in the drawing as well as in the claims can be critical for realizing the various embodiments of the invention.

We claim:

1. Supporting grid for the mechanical support of a cover membrane covering a bone void filled with a bone replacement material including hydroxyl apatite granules, said void including a recess in the proper bone tissue of the body, the improvement comprising said supporting grid having an outside contour of an annular sector with an outside arc and an inside arc, said supporting grid being bendable in a direction parallel to a surface normal of the supporting grid in an original condition around at least one line, which is located in a plane of the supporting grid, said grid having recesses along the inside arc and along the outside arc with each of the recesses at the inside arc having a narrow channel extending radially inward from the inside arc, then expanding slightly in a circular fashion and then in turn tapering down to a minimum width channel again over a small region and then expanding greatly and subsequently tapering conically.

2. Supporting grid according to claim 1, wherein the recesses along the inside arc are preferably arranged offset relative to the recesses along the outside arc.

3. Supporting grid according to claim 1, wherein the recesses along the inside arc and the recesses along the outside arc respectively have a uniform shape.

4. Supporting grid according to claim 1, wherein the shape of the recesses along the inside arc differs from the shape of the recesses along the outside arc.

5. Supporting grid according to claim 1, wherein each of the recesses has a radial symmetry axis.

6. Supporting grid according to claim 5, wherein the recesses at the inside arc transverse to the radial symmetry axis in the immediate proximity of said inside arc are broader than the recesses at the outside arc in the immediate proximity thereof.

7. Supporting grid according to claim 1, wherein the bases of the conical sections of the recesses at the inside arc are preferably located on nearly the same radius as the tips of the conical sections of the recesses at the outside arc.

8. Supporting grid according to claim 1, wherein the supporting grid has sub-recesses along the inside and outside arc that are open toward the outside contour.

9. Supporting grid according to claim 1, wherein each of the recesses along the outside arc having a triangular portion with a point directed toward the inside arc and a base of the triangular portion being connected to the outside arc by a narrow channel.

10. Supporting grid for the mechanical support of a cover membrane covering a bone void filled with a bone replacement material including hydroxyl apatite granules, said void including a recess in the proper bone tissue of the body, the improvement comprising said supporting grid having an outside contour of an annular sector with an outside arc and an inside arc, said supporting grid being bendable in a direction parallel to a surface normal of the supporting grid in an original condition around at least one line concentric with the outside arc and being located in a plane of the supporting grid, said supporting grid having recesses along the inside arc with each recess having a circular portion connected to the inside arc by a narrow channel and a triangular portion having a point directed at the outside arc and a base connected by a second channel portion to the circular portion and said grid having recesses along the outside arc.

11. Supporting grid according to claim 10, wherein the recesses along the inside arc are arranged offset relative to the recesses along the outside arc.

12. Supporting grid according to claim 10, wherein the recesses along the inside arc and the recesses along the outside arc respectively have a uniform shape.

13. Supporting grid according to claim 10, wherein the shape of the recesses along the inside arc differs from the shape of the recesses along the outside arc.

14. Supporting grid according to claim 10, wherein each of the recesses has a radial symmetry axis.

15. Supporting grid according to claim 14, wherein the recesses at the inside arc transverse to the radial symmetry axis in the immediate proximity of said inside arc are broader than the recesses at the outside arc in the immediate proximity thereof.

16. Supporting grid according to claim 10, wherein each of the recesses at the outside arc has a triangular portion with a point directed toward the inside arc and a base connected by a channel to the outside arc.

17. Supporting grid according to claim 10, wherein the recesses of the outside arc have a conical portion with a tip directed at the inside arc and a radius and the bases of the triangular portion of the recesses at the inside arc are located adjacent said radius.

18. Supporting grid according to claim 10, wherein the supporting grid has sub-recesses along the inside and outside arc that are open toward the outside contour.

* * * * *